United States Patent [19]

Hanson

[11] 4,060,083

[45] Nov. 29, 1977

[54] PILL GUN

[76] Inventor: Raymond L. Hanson, State Highway 8, Lindstrom, Minn. 55045

[21] Appl. No.: 672,799

[22] Filed: Apr. 1, 1976

[51] Int. Cl.² ............... A61D 7/00; A61M 31/00
[52] U.S. Cl. .................... 128/223; 128/264; 128/217
[58] Field of Search ............ 128/271, 264, 263, 217, 128/1.2, 222, 223

[56] References Cited

U.S. PATENT DOCUMENTS

| 2,601,852 | 7/1952 | Wendt | 128/264 |
| 2,647,512 | 8/1953 | Johnson | 128/264 |
| 2,754,822 | 7/1956 | Emelock | 128/264 |
| 3,753,437 | 8/1973 | Hood | 128/263 |
| 3,780,735 | 12/1973 | Crouter | 128/223 |
| 3,921,632 | 11/1975 | Bardani | 128/217 |

FOREIGN PATENT DOCUMENTS

| 649,002 | 9/1962 | Canada | 128/264 |
| 423,181 | 12/1925 | Germany | 128/264 |

Primary Examiner—Aldrich F. Medbery
Attorney, Agent, or Firm—H. Dale Palmatier

[57] ABSTRACT

A hand held pill gun for administering medicinal pills and capsules to small animals including a plastic barrel and plunger, and rigid broad surface manipulating bars on the barrel and spaced apart to bear firmly against the front and rear surfaces of the person's fingers.

6 Claims, 3 Drawing Figures

PILL GUN

BACKGROUND OF THE INVENTION

The problem of administering pills and capsules to animals has been previously recognized and pill guns of various sorts have been devised. However, taking into consideration that the person who is administering the pills or capsules must also use his other hand to hold the animal's mouth open and hold its head in the proper position, such prior devices have been uniformly deficient in their construction which does not permit careful and precise manipulation of the tool so that the pill gun can be quickly inserted into the animal's mouth at the opportune moment. It will be understood that all animals can be very quick, particularly when a person is attempting to administer medications, and requiring the animal to open its mouth. The teeth of a cat are extremely sharp, and if the pill gun cannot be promptly inserted into the cat's mouth at the opportune moment, the cat may very well move its head quickly and sink its teeth into the hand of the person attempting to administer the medication.

Prior pill dispensing guns have had protruding finger grips, and in some instances rings, but these devices have proved quite unsuccessful for giving the thorough control of the device which is required for the successful use of it.

BRIEF SUMMARY OF THE INVENTION

The present invention relates to a pill gun which is particularly adapted for administering medicinal pills and capsules to small animals such as cats, and constructed so that the pill gun may be quickly and accurately manipulated by the fingers of a person's hand to the extent that the pill gun seems to be an extension of the person's own hand. In the use and manipulation of the pill gun, no particular concentration may be directed to the mere holding of the pill gun, but the person using it need merely direct his attention to where exactly he desires to have the end of the pill gun at any particular moment.

The pill gun is accurately held and controlled by transverse manipulating bars which are mounted on the barrel and which provide broad, flat surfaces bearing against and tightly gripping the front and back surfaces of the person's fingers. The manipulating bars protrude outwardly from the barrel in both directions a distance which is on the same order as the spacing between the two transverse bars so that substantially the entire width of the person's finger is confined between the confronting manipulating bars.

Both of the manipulating bars may be adjustable along the barrel so that the location of them and their spacing from each other can be suitably adjusted, according to the desires of the person using the device and according to the size of his hand.

Of course, the position of the manipulating bars will depend somewhat on the type and size of animals with which the pill gun is being used.

Although the pill gun might be made of any of a number of materials, it has been found that a hard and fairly rigid plastic such as polypropylene is very successful. The several parts of the pill gun can be separately molded and quickly assembled.

DETAILED DESCRIPTION OF THE INVENTION

Figure 1:
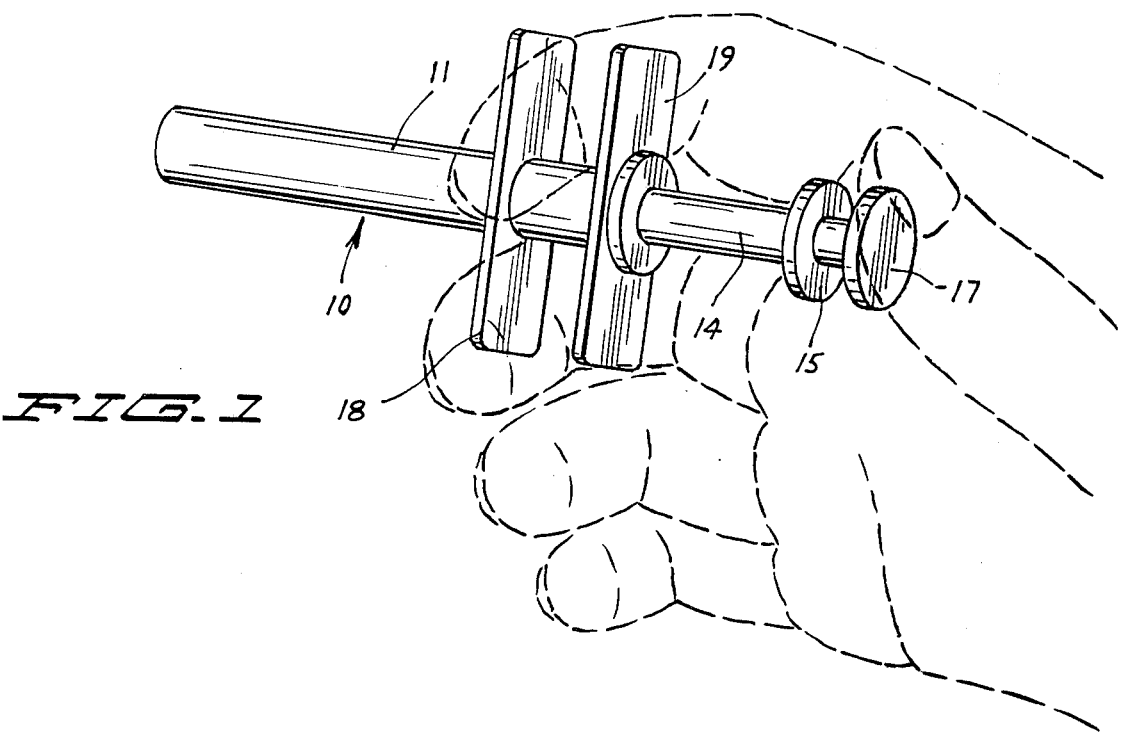
FIG. 1 is a perspective view of the pill gun and showing, in dotted lines, a person's hand being used for manipulation of it.

One form of the invention is shown in the drawings and is described herein. The pill gun is indicated in general by numeral 10 and includes a cylindrical barrel 11 with an open interior 12 defining a cylindrical chamber or cavity to confine one or more pills or capsules 13 therein.

A plunger 14 protrudes into the barrel and is slidable therein. The plunger is sufficiently long so that its forward end will extend entirely to the open forward end of the barrel so that the pills contained in the barrel can be positively ejected. The plunger 14 has a circular flange 15 formed integrally thereof to constitute a stop to engage against the flange 16 formed integrally of the barrel 11 at the upper or rear end thereof. A thumb piece or button 17 is also formed integrally of the piston or plunger 14 to provide a comfortable bearing surface against which a person's thumb or hand may bear when the pill 13 is being ejected.

Figure 2:
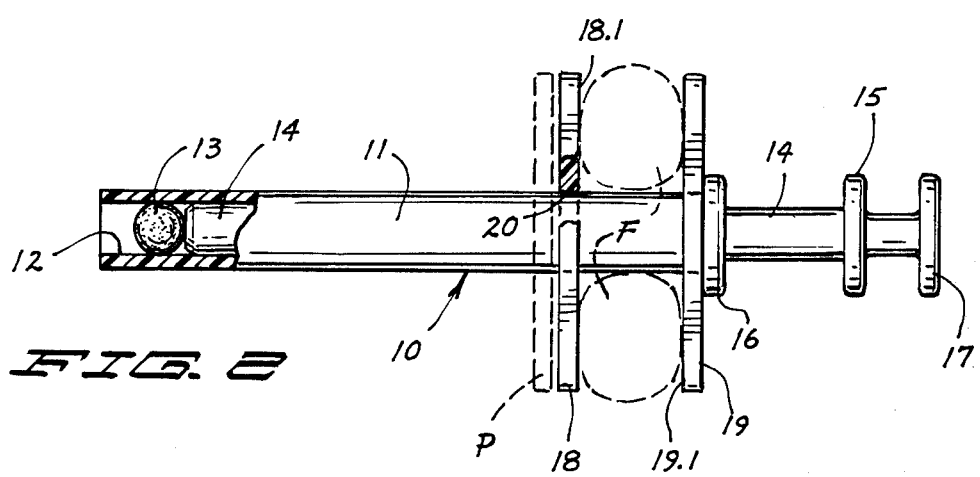
FIG. 2 is a side elevation view, with portions thereof broken away for clarity of detail.
Figure 3:
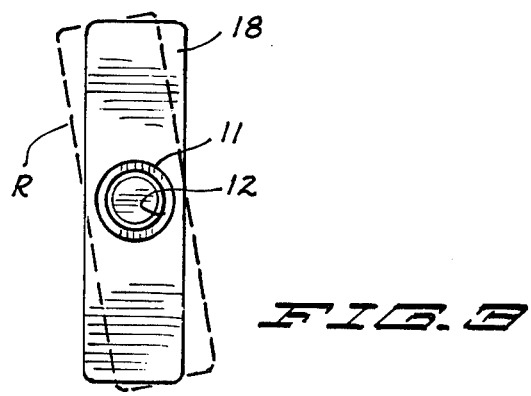
FIG. 3 is an end elevation view.

The pill gun 10 also has a pair of broad-surfaced manipulating bars 18 and 19 which are substantially identical to each other and which are essentially rigid and firmly mounted on the barrel 11. Each of the bars 18 and 19 has a central bearing aperture 20 receiving the barrel 11 therethrough and fitting with the barrel in a snug friction fit so that, under normal circumstances of use of the pill gun, the bars 18 and 19 will be stationary on the barrel 11, but the bars may be adjusted or moved along the barrel and around the barrel to desired position. An alternate adjusted position P of bar 18 is illustrated in FIG. 2, and a slightly rotated position R of the bar 18 is illustrated in FIG. 3.

It will be noted that the bars 18 and 19 extend transversely outwardly from the barrel 11 in both directions a distance which is approximately equal or of the order of the spacing between the two bars 18 and 19 so that the bars 18 and 19 extend substantially entirely across the front and rear faces of the person's fingers F will bear flush against the flat confronting surfaces 18.1 and 19.1 of the bars.

It should be noted that all of the parts of the pill gun, the barrel 11, plunger 14, and the bars 18 and 19, are preferably formed of a stiff and rather rigid plastic material such as polypropylene. Although the front end of the barrel 11 is illustrated to have a cylindrical interior for pill 13, the interior may be slightly elliptical in shape so that the barrel may, if slightly yieldable, accommodate and grip pills of various sizes. This would necessitate having the wall of the barrel sufficiently thin so that it may flex slightly, but this flexing may be accommodated without seriously weakening the barrel for the purpose intended.

In the use and operation of this pill gun, it will be understood that, in most cases, the pill 13 will be inserted into the end of the gun and the pill gun will be held in the person's hand such that the confronting broad flat surfaces 18.1 and 19.1 will bear flush against both the front and rear faces of the person's fingers F. It has been found highly preferable that the fingers F be inserted between the bars 18 and 19 so that the bars will engage the fingers between the first and second joints. In this position, the pill gun is very highly maneuverable, both by swinging the two fingers to a more nearly straightened position or to a position wherein such fingers more nearly form a tightly clenched fist of the person's hand. With such maneuvering, the barrel of the pill gun will move in a substantially horizontal plane.

Similarly, the barrel may be readily swung in a vertical plane by simply manipulating the fingers slightly between the bars 18 and 19, and, of course, any combination of these various manipulations will cause an appropriate motion of the barrel. In the administering of the medicinal pill to the animal, the pill gun will be so firmly attached to the fingers of the person's hand, that no particular attention need be given to holding the pill gun, and the entire concentration need only be directed to the insertion of the end of the barrel in the proper location of the animal's mouth.

It will be seen that I have provided a new and improved pill gun for administering medicinal pills and capsules to small animals such as cats and wherein the barrel and the entire pill gun can be readily and easily maneuvered by reason of its close gripping relationship on two fingers of a person's hand by broad and flat surfaces of the manipulating bars which are adjustably secured on the barrel of the gun.

What is claimed is:

1. A hand held pill gun for administering medicinal pills and capsules to small animals such as cats, comprising:

an elongate and stiff barrel having an open and blunt front end to receive and carry such a pill therein;

a pill discharging plunger slidable in the barrel to engage and eject the pill and having a thumb piece adjacent the rear end of the barrel for moving the plunger and pill; and means for holding the fingers of the hand in close grasping contact with the barrel while administering such pills and comprising a pair of broad surfaced manipulating bars mounted on the barrel adjacent the rear end thereof, said bars extending transversely of the barrel and outwardly from the barrel in both directions and in planes lying transversely of the longitudinal center line of the barrel, each of the bars having a breadth of the same order as the width of the barrel, the bars being spaced from each other on the barrel and having broad flat surfaces confronting each other to bear against and grip the front and rear faces of adjacent fingers of the hand for efficient manipulation of the gun, one of the bars movably and snugly engaging the barrel and being forcibly movable longitudinally along the barrel to hold the fingers on the barrel.

2. The pill gun according to claim 1, and the bars extending from the barrel in each direction a distance of the same order as the spacing between the bars.

3. The pill gun according to claim 2, and one of the bars being rotatably adjustable around the barrel to various angles.

4. The pill gun according to claim 1, and both of the bars being movable along the barrel and engaging the barrel in tight fitting frictional relation.

5. The pill gun according to claim 2 and the plunger having a pair of thumb pieces adjacent each other and adjacent the rear end of the barrel, the thumb pieces projecting transversely outwardly from the plunger for simultaneously engaging opposite sides of a person's thumb to facilitate sliding the plunger in either inward or outward directions.

6. A hand held pill gun for administering medicinal pills and capsules to small animals such as cats, comprising:

an elongate stiff barrel having an open front end to receive and carry such a pill therein;

a pill discharging slider in the barrel to engage and eject the pill and having a rear end exterior of the barrel with a pair of closely spaced and transversely oriented discs thereon to receive a portion of a person's thumb therebetween and for simultaneously engaging opposite sides of the thumb; and means for holding the fingers in close grasping contact with the barrel while administering said pills and comprising a pair of broad-surfaced manipulating bars mounted on the barrel adjacent the rear end thereof, said bars extending transversely of the barrel and outwardly from the barrel in both directions a distance of the same order as the spacing between the bars, the bars being spaced from each other on the barrel with the flat and broad-surfaced sides of the bars confronting each other to bear against and grip the front and rear faces of the adjacent fingers of the hand for efficient manipulation of the barrel and plunger without requiring convergent pressure to be exerted by the fingers against the barrel, the bars being spaced from each other a distance of the same order as the width of the barrel, one of the bars movably and frictionally gripping the barrel but being forcibly movable longitudinally along the barrel to change the spacing between the confronting flat sides of the bars to hold the fingers on the barrel.

* * * * *